United States Patent [19]

Thompson et al.

[11] Patent Number: 5,500,297
[45] Date of Patent: Mar. 19, 1996

[54] ELECTRON ACCEPTOR COMPOSITIONS TECHNICAL FIELD

[75] Inventors: Mark E. Thompson, Hamilton Square; Jonathan L. Snover, Mercerville, both of N.J.; Lori A. Vermeulen, Easton, Pa.

[73] Assignee: The Trustees of Princeton University, Princeton, N.J.

[21] Appl. No.: 103,968

[22] Filed: Aug. 9, 1993

[51] Int. Cl.⁶ .................................................. B32B 33/00
[52] U.S. Cl. ........................ 428/411.1; 544/225; 544/226; 546/213
[58] Field of Search ...................... 428/411.1; 544/225, 544/226; 546/213

[56] References Cited

U.S. PATENT DOCUMENTS

| | | | |
|---|---|---|---|
| 4,439,302 | 3/1984 | Wrighton et al. | 204/290 R |
| 4,473,695 | 9/1984 | Wrighton et al. | 546/266 |
| 4,721,601 | 1/1988 | Wrighton et al. | 422/68 |
| 4,895,705 | 1/1990 | Wrighton et al. | 422/68 |
| 5,034,192 | 7/1991 | Wrighton et al. | 422/82.02 |

OTHER PUBLICATIONS

M. B. Dines et al. "Mixed–Component Layered Tetravalent Metal Phosphonates/Phosphates as Precursors for Microporous Materials", 22 Inorg. Chem. 1003 (1983).

Vermeulen, Lori A., "Stable photoinduced charge separation in layered viologen compounds", Nature vol. 358 p. 656 Aug. 1992.

Primary Examiner—Paul J. Thibodeau
Assistant Examiner—David J. Abraham
Attorney, Agent, or Firm—Mathews, Woodbridge & Collins

[57] ABSTRACT

Stable electron acceptor compositions are composed of a plurality of pillared metal complexes disposed on a supporting substrate. At least one Group VIII metal at zero valence is entrapped within this matrix. The complexes comprise from one to about 100 units of the formula:

$$-(Y^1O_3-Z-Y^2O_3)Me^1-$$

$Y^1$ and $Y^2$ being phosphorus or arsenic; Z being a divalent group which reversibly forms a stable reduced form and contains two conjugated cationic centers having a negative $E°_{red}$ value; and $Me^1$ being a trivalent or tetravalent metal of Group III, IVA, or IVB having an atomic number of at least 21 or a lanthanide. The units are bound to the substrate through a divalent linking group. Counter anions balance the charge of Z. The compositions can be used in the decomposition of water to yield hydrogen gas, the sensing of oxygen, and as catalysts.

39 Claims, 2 Drawing Sheets

1

ELECTRON ACCEPTOR COMPOSITIONS

TECHNICAL FIELD

This invention was made with government support under grant number DMR-9113002, awarded by the National Science Foundation. The government has certain rights in this invention.

The present invention pertains to stable electron acceptor compositions which have efficient and sustained photoinduced charge separation states.

BACKGROUND OF THE INVENTION

Solar energy can be used and stored by the efficient production of long-lived photo-induced charge separation—a state achieved in photosynthetic systems by the formation of a long-lived radical pair. A number of artificial systems have been reported that efficiently undergo photochemical charge transfer, unfortunately, the thermal back electron transfer often proceeds at an appreciable rate, limiting the utility of these systems. What is needed is a systems which has very efficient photoinduced charge transfer, and forms a charge-separated state which is long lived in air. The charge separation in these systems typically involves a redox reaction between a photoexcited donor and a suitable acceptor, resulting in the production of radical ion pairs illustrated by the formula:

$$D + h\nu \rightarrow D^* \quad (1a)$$

$$D^* + A \rightarrow A^- \quad (1)$$

$$D^+ + A^- \rightarrow D + A \quad (2)$$

The cation and anion generated in this way are better oxidants and reductants, respectively, than either of the neutral groundstate molecules. To harvest the light put into this system, the oxidizing and reducing power of the photogenerated species must be used before the electrons are transferred back (equation 2) generating the starting materials. It is desirable to control this photochemically unproductive thermal fast back electron transfer reaction. One method has been to incorporate the donors and acceptors into solid matrices.

It is one objective of the present invention to provide compositions having efficient and sustained photoinduced charge separation states.

SUMMARY OF THE INVENTION.

This photoinduced charge separation renders the compositions useful in solar energy conversion and storage. In addition, the compositions permit reduction of various metal ions to produce the zero-valence metal in colloidal form entrapped in the matrices of the compositions. These latter matrices containing the zero-valence metal have a variety of uses such as in the decomposition of water to yield hydrogen gas and the sensing of oxygen. In addition, the zero-valence metal matrices can be used in catalysis, as for example in the production of hydrogen peroxide and the oligomerization of methane to form higher hydrocarbons.

DESCRIPTION OF THE PREFERRED EMBODIMENT

Figure 1:
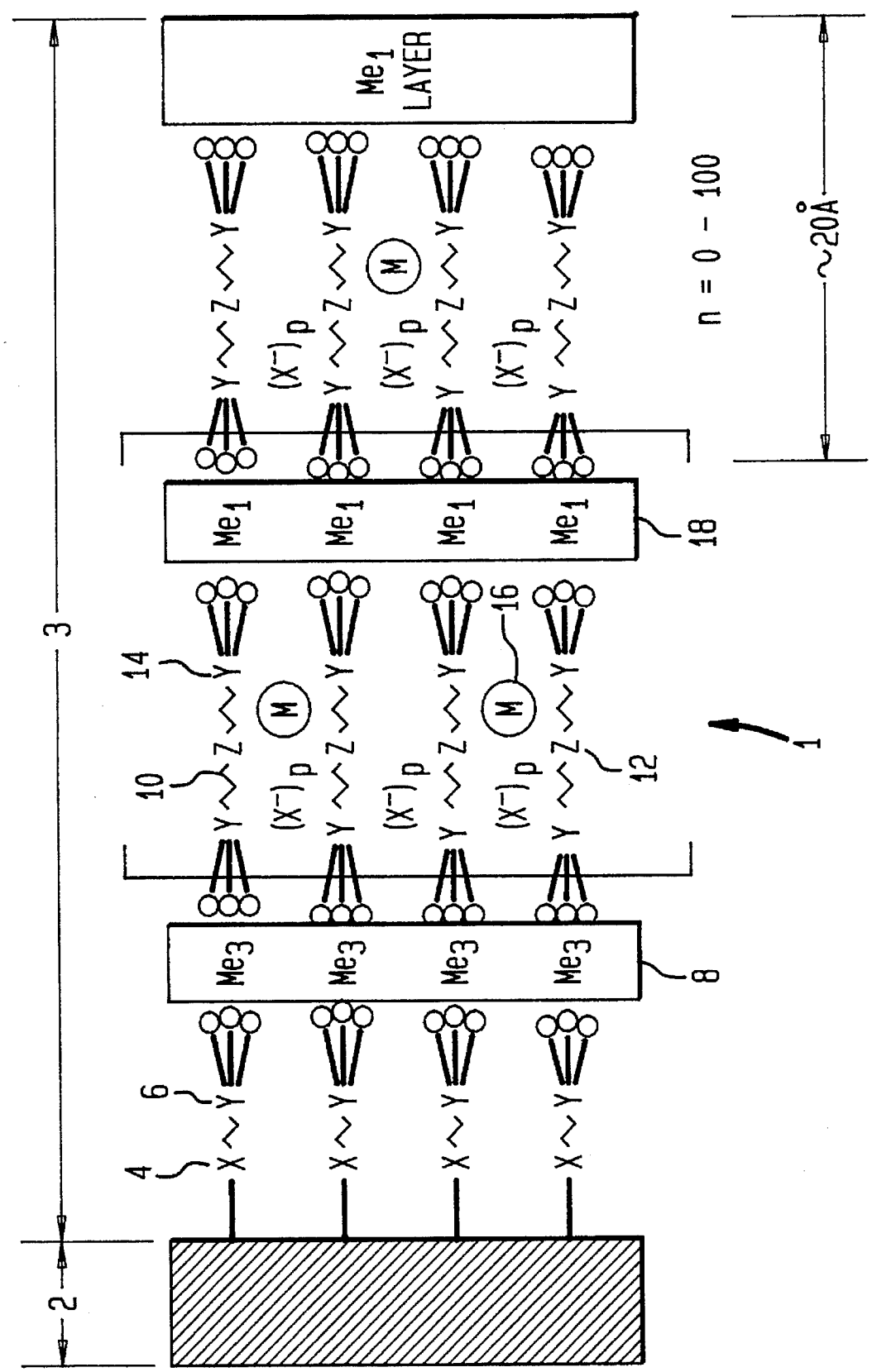
FIG. 1 is a schematic view of the highly ordered structure of a substrate and film according to the present invention.

In particular, the invention relates in a first embodiment to a composite composition in which a film is disposed on a supporting substrate. The film is composed of a plurality of pillared metal complexes, each of the formula:

$$-O-L-[(Y^1O_3-Z-Y^2O_3)Me^1]_k \cdot k^*p(X^{2/p-}) \quad \text{I.}$$

in which:

L is a divalent linking group; each of $Y^1$ and $Y^2$, independently of the other is phosphorus or arsenic;

Z is a divalent group which reversibly forms a stable reduced form and contains two conjugated cationic centers which together have a negative $E°_{red}$ value;

$Me^1$ is a trivalent or tetravalent metal of Group III, IVA, or IVB having an atomic number of at least 21 or a lanthanide;

X is an anion;

k has a value of from 1 to about 100; and p has a value of 1 or 2.

$Me^1$ can be, for example, a group IVA metal having an atomic number of at least 21 such as germanium, tin, or lead, a group IVB metal such as titanium, zirconium, or hafnium, a group IIIA metal having an atomic number of at least 21 such as gallium, indium, or thallium, a group IIIB metal such as scandium, yttrium, or a lanthanide as for example lanthanum, cerium, praseodymium, etc. Of these, titanium, zirconium, hafnium, germanium, tin, and lead are preferred with zirconium being particularly useful.

Each of $Y^1$ and $Y^2$ is phosphorus or arsenic, preferably phosphorus, each of $Y^1O_3$ and $Y^2O_3$ thus being a phosphonato or arsonato group.

The group Z is divalent, being bound to the phosphorus or arsenic atom of the phosphonato or arsonato group defined by $Y^1O_3$ and $Y^2O_3$. In practice, the precise structure of the group Z is of lesser importance than its electronic properties. Firstly, it must contain two conjugated cationic centers which together have a negative $E°_{red}$ value; i.e., a reduction potential below that of hydrogen. Secondly, Z must be capable of existing both in a stable reduced form and reversibly in an oxidized form.

The two conjugated cationic centers can be for example tetravalent nitrogen atoms which are conjugated ring members in an aromatic ring system.

In one embodiment, each tetravalent nitrogen atom is a ring member in a separate aromatic ring system and two such ring systems, which can be of the same or different structure, are joined to one another directly through a covalent bond. Each such aromatic ring system can be a monocycle such as pyridine, pyrazine, or pyrimidine. Alternatively, each aromatic ring system can be a fused polycycle in which a pyridine, pyrazine, or pyrimidine ring is fused to one or more benzo or naphtho ring system, as for example quinolinium, isoquninolinium, phenanthridine, acridine, benz[h]isoquinoline, and the like.

The two aromatic ring systems, which can be of the same or different structure, alternatively can be linked through a divalent conjugated system as for example diazo (—N=N—), imino (—CH=N—), vinylene, buta-1,3-diene-1,4-diyl, phenylene, biphenylene, and the like.

In a further embodiment, the two conjugated cationic centers can be in a single aromatic system such as phenanthroline, 1,10-diazaanthrene, and phenazine.

Typical dicationic structures suitable as Z thus include 2,2-bipyridinium, 3,3-bipyridinium, 4,4-bipyridinium, 2,2-bipyrazinium, 4,4-biquinolinium, 4,4-biisoquninolinium, 4-[2-(4-pyridinium)vinyl]pyridinium, and 4-[4-(4-pyridinium)phenyl]pyridinium.

The aromatic systems in which the two conjugated cationic centers are located can be unsubstituted or substituted, as for example with alkyl of 1 to 6 carbon atoms or alkoxy of 1 to 6 carbon atoms. Such substitution can be inert or can have an effect on the reduction potentials of the cationic centers sterically or through induction.

While the two cationic centers must be linked through conjugation, the entire system comprised by Z need not be conjugated. Thus Z can be joined to each of $Y^1O_3$ and $Y^2O_3$ through a conjugated or non-conjugated bridge. Hence one highly desirable structure for Z is characterized by the structure:

$$—(R^1)_n—Z'—(R^2)_m—\qquad\qquad\text{II.}$$

in which Z' is a divalent aromatic group containing at least two conjugated tetravalent nitrogen atoms; each of n and m, independently of the other, has a value of 0 or 1; and each of $R^1$ and $R^2$, independently of the other is a divalent aliphatic or aromatic hydrocarbon group. Typically each of n and m will be 1 and each of $R^1$ and $R^2$, independently of the other, will be a straight or branched divalent alkane chain of six or less carbon atoms, as for example methylene, ethano, trimethylene, propane-1,2-diyl, 2-methylpropan-1, 2-diyl, butane-1,2-diyl, butane-1,3-diyl, tetramethylene, and the like.

The group X is an anionic group one or more of which (depending on the value of k and the charge of X) will balance the cationic charges of Z. The precise nature of X is relatively unimportant and X can be for example a halogen anion such as chloride, bromide, iodide, a pseudohalide, sulfate, sulfonate, nitrate, carbonate, carboxylate, etc.

The composition 1 comprises a supporting substrate 2 to which is bound a film 3 comprising a molecular plurality of the complexes of Formula I. Thus each complex depicted by Formula I is bound to the substrate through the depicted univalent oxygen atom. There is a molecular plurality of —L—Zr—$Y^1O_3$—Z—$Y^2O_3H_2$•2X' units on a given substrate, thereby producing a pillared structure, as illustrated in FIG. 1.

Each complex can contain one Z-containing unit 12, in which case k has a value of 1, but preferably k has a value in excess of 1 so that the unit —($Y^1O_3$—Z—$Y^2O_3$)Me$^1$— becomes the monomer of the pillared polymeric complex in which k ranges from 2 to about 100, typically from about 5 to about 50.

Such films are prepared through sequential adsorption reactions analogously to those described by Rong et al., *Coordination Chemistry Reviews*, 97, 237 (1990). Thus the substrate, which typically is hydroxy terminated, as for example metals (the surfaces of which invariably include the metal oxide), glass, silicas, gallium arsenide, and the like, is first derivatived with a hydroxy-reactive reagent which introduces the linking group L or components of that linking group. Typically the distal portion of L will terminate in, and thus eventually be bound to $Y^1O_3$ through, a metal atom Me$^3$ 8 which is similar to Me$^1$, i.e. a trivalent or tetravalent metal of Group III, IVA, or IVB having an atomic number of at least 21, or a lanthanide.

Thus for example, the substrate can be treated with a compound of the formula:

$$X''—R^1—Z—Y^3O_3H_2•2X'\qquad\qquad\text{III.}$$

in which $R^1$ and Z are as herein defined; $Y^3$ is phosphorus or arsenic; X' is an anion analogous to X (X' can be, but need not necessarily be, the same anion as will appear in the final complex) and X" is a reactive halogen such as chloro or bromo. Thereby produced is the intermediate:

$$\text{substrate}—O—R^1—Z—Y^3O_3H_2•2X'\qquad\qquad\text{IV.}$$

The foregoing reactions can be conducted in two stages, first by treating the substrate with a compound of the formula X"—$R^1$—Z•2X' and then treating the product with a phosphoryl halide such as phosphoryl chloride or phosphoryl bromide or a corresponding arsonyl halide.

In either aspect of this embodiment, the linking group produced is similar to the repeating unit insofar as it contains —Z—$Y^3O_3$.

Alternatively, the linking group can be dissimilar to the repeating unit. Thus the substrate can be treated with a silane such as an aminoalkyltrialkoxysilane as for example 3-aminopropyltriethoxysilane and this derivatived substrate then treated with a phosphoryl halide such as phosphoryl chloride or phosphoryl bromide or a corresponding arsonyl halide to produce:

$$\text{substrate}—O—\text{alkyl}—Y^3O_3H_2.\qquad\qquad\text{V.}$$

In either case, the intermediate having a surface rich in phosphonate or arsonate groups then is treated with a reagent providing Me$^3$ ions, e.g., zirconyl chloride. The metal ions bind to the phosphonate groups, in turn producing an intermediate having a metal rich surface and characterized as "substrate-L'" in which L' corresponds to the linking group of Formula I (but terminates in Me$^3$).

The precise chemical composition of L, and thus L', is relatively unimportant since it need only provide a link which (i) on the one hand binds to hydroxy groups on the substrate and (ii) on the other presents a metal Me$^3$ for further complexing.

The substrate-L' with the linking group bound to it then is separated from the reagent providing Me$^3$ ions, washed with water, and treated with a solution of a bisphosphonic acid or bisarsonic acid of the formula:

$$H_2Y^1O_3—Z—Y^2O_3H_2•2X'\qquad\qquad\text{VI.}$$

in which $Y^1$, $Y^2$, Z and X' are as defined above. This reaction is complete within a few hours, as for example about 4 to 5 hours, and can be accelerated through the use of moderate heat, as for example from about 80° to about 100° C. The deposition of this layer can be readily monitored spectrophotometrically at wavelengths of from about 260 to about 285 nm. For consistency, generally the range of 280–285 nm is employed. One of the —$Y^1O_3H_2$ and —$Y^2O_3{}^H{}_2$ groups binds to the zirconium rich surface, while the other remains uncoordinated, thereby now producing an intermediate having a surface rich in phosphonate or arsonate groups. This intermediate can be depicted as:

$$\text{substrate}—O—L—Zr—Y^1O_3—Z—Y^2O_3H_2•2X'\qquad\qquad\text{VII.}$$

The substrate—O—L—Zr—$Y^1O_3$—Z—$Y^2O_3H_2$•2X' is removed from the solution of the bisphosphonic acid or bisarsonic acid, rinsed thoroughly, and then treated with a reagent providing Me$^1$ 18 ions to produce a complex of Formula I in which k is 1.

The foregoing sequence of the last two synthetic steps, that is treatment with a bisphosphonic acid or bisarsonic acid followed by treatment with a reagent providing Me¹ ions, is repeated to produce complexes having higher k values. Absorbance, as for example at 280–285 nm, appears to increase linearly with the number of layers and provides a convenient method of monitoring the formation of multilaminar compositions.

The foregoing procedure is readily modified to entrap atoms of at least one Group VIII metal 16, as for example platinum, palladium, iron, cobalt, nickel, ruthenium, rhodium, osmium, or iridium, at zero valence within the complexes. Thus following treatment with a bisphosphonic acid or bisarsonic acid but before treatment with a reagent providing Me¹ ions, the sample is immersed in an aqueous solution of a soluble anionic salt of the Group VIII metal. After a short time, the metal anion exchanges with some of the chloride anions in the sample. The stoichiometrics of this exchange will depend upon the respective valences of the two anions. The platinum tetrachloride and platinum hexachloride anions, for example, each have a valence of −2 and if chloride were the starting anion, one anion of either of these metal anions would exchange for two chloride anions.

Following this exchange, treatment with a reagent providing Me¹ ions then is performed as described above. As above, these reactions are repeated until the desired k value is attained. The composite is then simply exposed to hydrogen gas which reduces the metal anion to produce the metal in a zero valence state and colloidal form within the matrix of the composite. As noted previously, such materials are highly effective as catalysts in the production of hydrogen peroxide, the oligomerization of methane to form higher hydrocarbons, the decomposition of water to yield hydrogen gas, and the sensing of oxygen. The compositions also can be utilized to reduce various organic substrates.

It is possible to utilize more than one Group VIII metal in any sample, either using soluble salts of different Group VIII metals in one or more exchanges or conducting one or more exchanges with a first Group VIII metal and subsequent exchanges with a different Group VIII metal. Thus created upon eventual reduction are unique compositions in which colloidal particles of two Group VIII metal having different chemical and electronic properties are entrapped in a single matrix.

In a second embodiment, the invention related to mixed complexes of the formula:

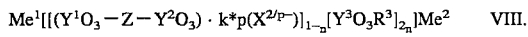

VIII.

wherein each of $Y^1$, $Y^2$, and $Y^3$, independently of the other, is phosphorus or arsenic;

Z is a divalent group which reversibly forms a stable reduced form, said group containing two conjugated cationic centers which together have a negative $E°_{red}$ value;

each of Me¹ and Me² is a trivalent or tetravalent metal of Group III, IVA, or IVB having an atomic number of at least 21 or a lanthanide;

X is an anion;

n has a value of from 0.1 to 0.8; and $R^3$ is a nonreducible capping group.

Figure 2:
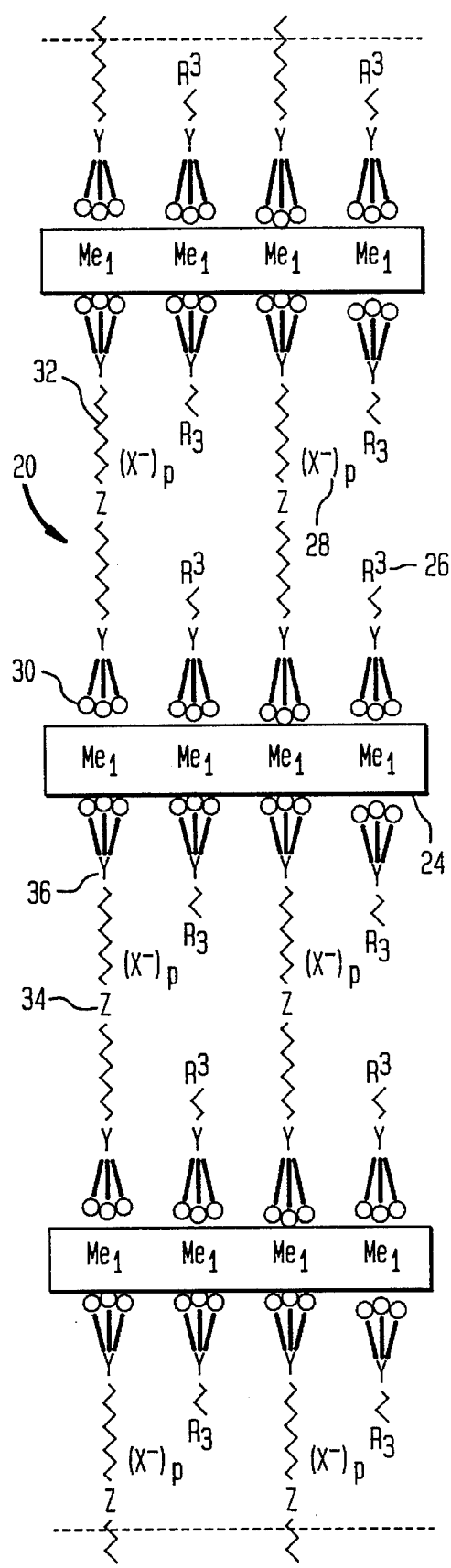
FIG. 2 is a schematic view of a solid composition according to the present invention.
Figure 3:
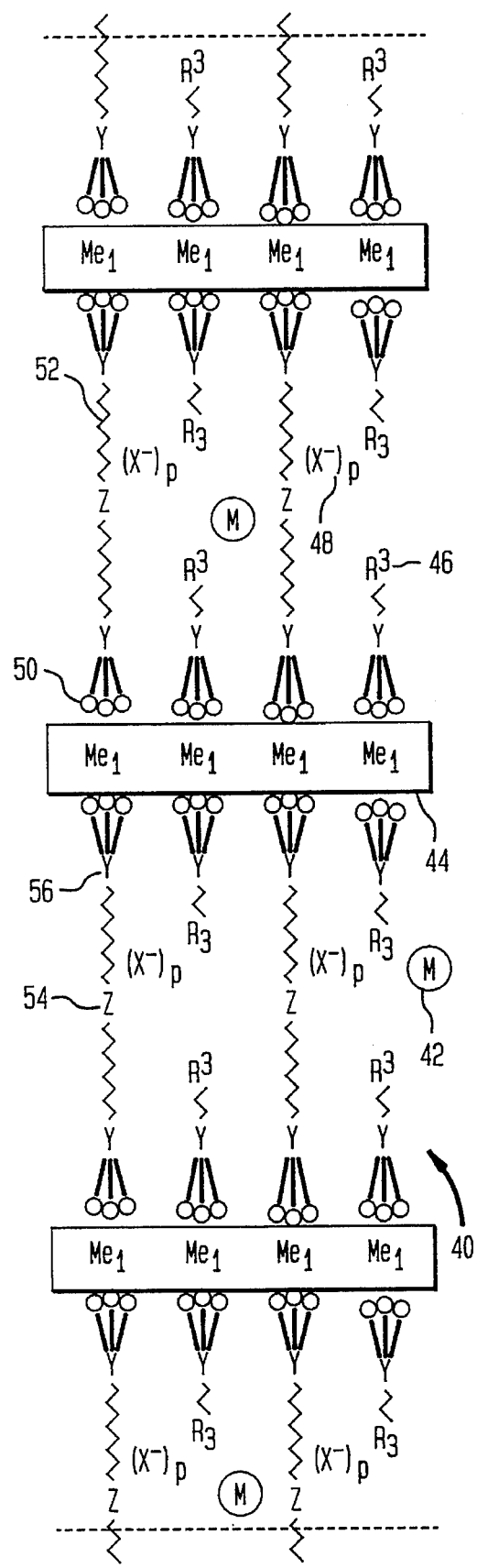
FIG. 3 is a schematic view of a solid of the present invention incorporating metal particles according to the present invention.

In contrast to the materials of the first embodiment which are films, there materials are crystalline or amorphous solids, as illustrated in FIGS. 2 and 3. Analogously to the films of the first embodiment, however, zero valence Group VIII metals 42 can be incorporated in these matrices.

As is apparent from Formula VIII, two distinct ligands complex the metals Me¹ and Me² 24,44. The first of these is analogous to that utilized in Formula I, namely $Y^1O_3$—Z—$Y^2O_3$, and each such ligand is capable of complexing with two metal atoms. The second ligand $Y^3O_3R^3$, 26, 46 is capable of complexing with only one metal atom. Thus the overall structure may be viewed as a series of parallel layers of the metals Me¹ and Me² with the $Y^1O_3$—Z—$Y^2O_3$ 30, 32, 34, 36 groups serving as pillars. Extending from the metal layers between these pillars are the $Y^3O_3R^3$ groups, forming as it were a series of "stalagtites" and "stalagmites" between the pillars.

The resultant structure thus has a series of interstices about each —Z— group. The dimensions of these interstices and the hydrophobicity of their defining surfaces can be controlled through selection of $R^3$. Thus one can select relatively small $R^3$ groups such as methyl, creating larger interstices, or relatively larger $R^3$ groups such as phenyl or benzyl, thereby producing relatively smaller interstices. Similarly, one can impart hydrophobic properties to the defining surfaces of the interstices by employing a hydrocarbon group such as propyl for $R^3$ or alternatively decrease the hydrophobicity by employing an $R^3$ group which is substituted with a hydrophilic group such as carboxy.

Because of these interstices, it is possible to introduce Group VIII metals after formation of the complexes, rather than after each step, and then reduce these to zero valence as described above. Hence a complex of Formula VIII is treated with an aqueous solution of a soluble anionic salt of a Group VIII metal and the resulting composition treated with hydrogen to produce the Group VIII metal in colloidal form. These compositions can be used as catalysts as previously described.

Moreover, these interstices permit the passage of various molecules into the complexes. For example, oxygen can enter into the matrices and then oxidize the —Z— groups. Since the reduced form of the —Z— group are colored while the oxidized form is white or yellow, this phenomenon can be used to detect oxygen at extremely low levels.

In addition, the ability to control the dimensions of the interstices permits the use of these materials in effecting selective reactions. For example, it is possible to selectively reduce acetophenone in a mixture of acetophenone and 3,5-di-tert. butylacetophenone if the dimensions of the interstices are selected to permit passage of the former molecule but not the latter, more bulky, molecule.

The complexes are readily prepared by treating a mixture of $R^3Y^3O_3H_2$ and $H_2Y^1O_3$—Z—$Y^2O_3H_2$ in the desired molar ratio with a source of metal ions. The reaction can be conducted either by refluxing or hydrothermally and the products are readily isolated and purified.

The following examples will serve to further typify the nature of the invention but should not be construed as a limitation on the scope thereof which is defined solely by the appended claims.

EXAMPLE 1

Diethyl 2-bromoethylphosphonate (25 g) and 4,4' bipyridine (7.35 g) in 125 mLs of water are refluxed for three days. An equal volume of concentrated hydrochloric acid is added and reflux continued for several hours. The solution is concentrated to 120 mLs by atmospheric distillation and 550 mL of isopropanol are added dropwise with stirring while chilling the mixture in an ice bath. The solid which forms is collected by vacuum filtration and washed with cold isopropanol to yield 1,1'-bisphosphonoethyl-4,4'-bipyridinium dichloride. (¹H NMR (D₂O) 9.1(d), 8.5(d), 4.2(m), 2.0(m) ppm; ¹³C NMR(D₂O) 151, 147, 128, 58, 30 ppm; ³¹P NMR(D$_2$O) 17.8 (s) ppm; IR (KBr) 3112, 3014, 1640, 1555, 1506, 1443, 1358, 1281, 1175, 1112, 1020, 936, 816, 485 cm$^{-1}$.)

In a similar fashion, utilizing 2,2-bipyridinium, 3,3-bipyridinium, 2,2-bipyrazinium, 4,4-biquinolinium, 4,4-biisoquninolinium, 4-[2-(4-pyridinium)vinyl]pyridinium, and 4-[4-(4-pyridinium)phenyl]pyridinium, there are respectively obtained 1,1'-bisphosphonoethyl-2,2-bipyridinium dichloride, 1,1'-bisphosphonoethyl-3,3-bipyridinium dichloride, 1,1'-bisphosphonoethyl- 2,2-bipyrazinium dichloride, 1,1'-bisphosphonoethyl-4,4-biquinolinium dichloride, 1,1'-bisphosphonoethyl-4,4-biisoquninolinium dichloride, 1-phosphonoethyl-4-[2-(1-phosphonoethyl-4-pyridinium)vinyl]pyridinium dichloride, and 1-phosphonoethyl-4-[4-(1-phosphonoethyl-4-pyridinium)phenyl]pyridinium dichloride.

Other cationic species, such as the corresponding dibromides or disulfates are obtained by substituting the corresponding acids, such as concentrated hydrobromic acid or sulfuric acid, for hydrochloric acid in the procedure of this example.

EXAMPLE 2

Planar substrates of fused silica (9×25 mm) are cleaned in a 1:3 solution of 30% hydrogen peroxide and conc. sulfuric acid, dried at 200° C. for one hour, and then treated with a refluxing solution of 2% (v/v) 3-aminopropyltriethoxysilane in 50 mL of octane for 20 minutes.

The substrates are rinsed with octane and acetonitrile and treated for 12 hours at room temperature with a solution of 10 mM each of phosphoryl chloride and 2,6-lutidine in acetonitrile. After rinsing in water, the substrates are treated with a 65 mM solution of zirconyl chloride for three hours at room temperature.

The foregoing procedure can be used to prepare multilayer films on other substrates such as silicon wafers and vapor deposited gold films.

The substrate next is subjected sequentially to the following two steps.

A. After removal of the solution of zirconyl chloride, the samples are thoroughly rinsed with deionized water and treated with 6 mM of 1,1'-bisphosphonoethyl-4,4'-bipyridinium dichloride at 80 C. for 4 hours and then thoroughly rinsed with deionized water. (Absorption is measured at 284 nm after treatment, the measured extinction coefficient for 4,4'-bipyridinium bisphosphonate being 24,000 M$^{-1}$ cm$^{-1}$ at 265 nm.)

B. The samples next are treated with a a 65 mM zirconyl chloride solution at room temperature for one hour and again thoroughly rinsed with deionized water.

Upon completion of one cycle of steps A and B, a plurality of a metal complex of Formula I in which k is 1 is obtained on the planar silica supporting substrate. Each repetition of steps A and B increases the value of k by one. The number of layers, and thus the number of cycles, correlates to absorbance at 284 nm, as can be seen from the following:

| No. of Layers | Absorbance |
|---|---|
| 0 | 0.057 |
| 1 | 0.083 |
| 2 | 0.091 |
| 3 | 0.109 |
| 4 | 0.130 |
| 5 | 0.152 |
| 6 | 0.177 |
| 7 | 0.201 |
| 8 | 0.217 |
| 9 | 0.242 |
| 10 | 0.263 |
| 11 | 0.281 |
| 12 | 0.299 |
| 13 | 0.327 |
| 14 | 0.341 |
| 15 | 0.357 |
| 16 | 0.367 |
| 17 | 0.373 |
| 18 | 0.383 |
| 19 | 0.407 |
| 20 | 0.423 |
| 21 | 0.452 |
| 22 | 0.458 |

EXAMPLE 3

By substituting 1,1'-bisphosphonoethyl-4,4'-bipyridinium dibromide in the procedure of Example 2, a series of multilaminar compositions are obtained having the following absorbances:

| No. of Layers | Absorbance |
|---|---|
| 1 | 0.083 |
| 2 | 0.098 |
| 3 | 0.113 |
| 4 | 0.157 |
| 5 | 0.182 |
| 6 | 0.239 |
| 7 | 0.286 |
| 8 | 0.350 |
| 9 | 0.353 |
| 10 | 0.391 |
| 11 | 0.465 |
| 12 | 0.557 |

EXAMPLE 4

High quality films also are obtained by employing other metals in place of zirconium in step B, e.g., hafnium, titanium, tin, gallium, etc, as shown in the following procedure.

Planar fused silica substrates (9×25 mm) are cleaned as described in Example 2 and a layer of 3-aminopropyltriethoxysilane is deposited thereon from the gas phase using the method of Haller, *J. Am. Chem. Soc.*, 100, 8050 (1978). The substrates are phosphorylated as described in Example 2, rinsed, and treated with 10 mL of a 65 mM aqueous solution of hafnyl chloride for three hours at room temperature.

Alternating treatments with (A) an aqueous solution containing 6 mM 1,1'-bisphosphonoethyl-4,4'-bipyridinium dibromide and 20 mM sodium chloride at 80 C. for 4 hours and (B) a 65 mM aqueous solution hafnyl chloride at room temperature for 1 hour, with thorough rinsing with deionized water after each, then produce a series of multilaminar compositions which can be characterized spectrophotometrically at 284 nm.

| No. of Layers | Absorbance |
|---|---|
| 1 | 0.052 |

| No. of Layers | Absorbance |
|---|---|
| 2 | 0.086 |
| 4 | 0.175 |
| 6 | 0.250 |
| 8 | 0.304 |
| 10 | 0.384 |
| 12 | 0.518 |

EXAMPLE 5

The procedure of Example 2 is modified after one or more executions of step A but before execution of the corresponding step B by immersing the samples in a 6 mM aqueous solution of dipotassium platinum tetrachloride for 0.5 hour thereby exchanging one platinum tetrachloride anion for two chloride anions. Step B then is performed as described in Example 2.

After completing the final cycle of steps A and B, the composite is suspended in water and hydrogen gas is bubbled through the mixture for two hours. The platinum is reduced to a zero valence colloidal state entrapped in the overall matrix.

EXAMPLE 6

Silica particles (1 g) are heated in a drying oven for one hour and then stirred with 150 mL of an aqueous solution (60 mM) of zirconyl chloride with the silica (1 g) at 60° C. for two days. The solid is isolated by filtration or centrifugation, washed three times with 150 mL of deionized water, and treated with 150 mL of a 20 mM solution of the 1,1'-bisphosphonoethyl-4,4'-bipyridinium for six hours at 65 C. with agitation. The solid is separated from the aqueous solution and washed three times with deionized water.

The solid then is treated with 150 mL of a 20 mM solution of potassium platinum hexachloride for three hours at room temperature, thereby exchanging one platinum hexachloride anion for two chloride anions.

One hundred and fifty milliliters of a 60 mM solution of zirconyl chloride are added to the solid and the slurry agitated for three hours at room temperature and washed three times with deionized water.

The foregoing steps are repeated four times to produce a pentalaminar composition containing platinum cations. Treatment of an aqueous slurry of the platinized materials with hydrogen then converts the platinum ions into colloidal zero valence platinum metal.

EXAMPLE 7

Zirconyl chloride octahydrate (1.444 g, 4.8 mmol.) is dissolved in 50 mLs water and 50% hydrofluoric acid (0.756 g, 19 mmol) are added. To this is added a solution of 1 g of 1,1'-bisphosphonoethyl-4,4'-bipyridinium dichloride (2.2 mmol) and 0.516 g of 85% phosphoric acid (4.5 mmol.) in 50 mLs of water. The reaction is refluxed for seven days and the white crystalline product is filtered and washed with water, methanol, and acetone and air-dried to yield the mixed complex:

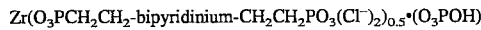

$Zr(O_3PCH_2CH_2\text{-bipyridinium-}CH_2CH_2PO_3(Cl^-)_2)_{0.5}\cdot(O_3POH)$

X-Ray diffraction analysis shows d=14 Å. Infra red analysis is as follows: (IR (cm−1), 3126, 3056, 1633, 1562, 1499, 1450, 1217, 1055, 816, 738, 647, 612, 520, 471). $^{31}P$ NMR (ppm) are: 3.0, −18.6, −24.5.

EXAMPLE 8

Zirconyl chloride octahydrate (0.21 g, 0.7 mmol.) is dissolved in 10 mLs water and 50% hydrofluoric acid (0.11 g, 2.8 mmol) are added. To this is added a solution of 0.15 g of 1,1'-bisphosphonoethyl-4,4'-bipyridinium dichloride (0.35 mmol) and 0.0686 g of 85% phosphoric acid (0.6 mmol.) in 10 mLs of water. The solution is placed in a 45 mL teflon bomb and the total volume adjusted to 27 mLs. The bomb is sealed and heated at 150° C. for six days to yield the mixed complex:

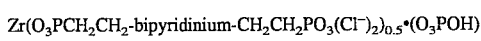

$Zr(O_3PCH_2CH_2\text{-bipyridinium-}CH_2CH_2PO_3(Cl^-)_2)_{0.5}\cdot(O_3POH)$

X-Ray diffraction analysis shows d=14 Å. Infra red and $^{31}P$ NMR (ppm) are identical to those given in Example 7.

EXAMPLE 9

Zirconyl chloride octahydrate (0.36 g, 1.12 mmol.) is dissolved in 10 mLs water and 50% hydrofluoric acid (0.179 g, 4.5 mmol) are added. To this is added a solution of 0.25 g of 1,1'-bisphosphonoethyl-4,4'-bipyridinium dichloride (0.56 mmol) and 0.129 g of 85% phosphoric acid (0.11 mmol.) in 50 mLs of 3N-hydrochloric acid. The reaction is refluxed for seven days and the white crystalline product is filtered and washed with water, methanol, and acetone and air-dried to yield the mixed complex:

$Zr(O_3PCH_2CH_2\text{-bipyridinium-}CH_2CH_2PO_3(Cl^-)_2)_{0.5}\cdot(O_3POH)$

X-Ray diffraction analysis shows d=18.5 Å. Infra red and $^{31}P$ NMR (ppm) are identical to those given in Example 7.

EXAMPLE 10

Zirconyl chloride (octahydrate) (0.361 g, 1.12 mmol.) is dissolved in 10 mLs water and 0.189 g of 50% hydrofluoric acid (4.8 mmol.) is added. 1,1'-Bisphosphonoethyl-bipyridinium dichloride (0.25 g, 0.56 mmol.) and phosphorous acid (0.092 g, 1.12 mmol.) are dissolved in 10 mLs of water and this solution is added to the aqueous zirconium solution. The reaction is refluxed for seven days and the white crystalline product is filtered, washed with water, methanol, and acetone and air-dried to yield the mixed complex:

$Zr(O_3PCH_2CH_2\text{-bipyridinium-}CH_2CH_2PO_3(Cl^-)_2)_{0.5}\cdot HPO_3$

X-Ray diffraction analysis shows d=18.4 Å. Infra red analysis is as follows: 3126, 3056, 2436, 2358, 2330, 1633, 1555, 1499, 1443, 1386, 1210, 1161, 1048, 830, 731, 548. $^{31}P$ NMR (ppm) are: 5.5, −9.5.

EXAMPLE 11

By following the procedure of Example 10 but utilizing 0.167 (0.38 mmol.) of 1,1'-bisphosphonoethyl-bipyridinium dichloride and 0.123 g (1.5 mmol.) of phosphorous acid, there is obtained the mixed complex:

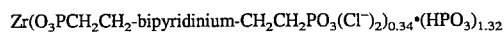

$Zr(O_3PCH_2CH_2\text{-bipyridinium-}CH_2CH_2PO_3(Cl^-)_2)_{0.34}\cdot(HPO_3)_{1.32}$ The material is amorphous. Infra red and $^{31}P$ NMR (ppm) are identical to those given in Example 10.

EXAMPLE 12

By following the procedure of Example 10 but utilizing 0.125 (0.28 mmol.) of 1,1'-bisphosphonoethyl-bipyridinium dichloride and 0.138 g (1.68 mmol.) of phosphorous acid, there is obtained the mixed complex:

$Zr(O_3PCH_2CH_2\text{-bipyridinium-}CH_2CH_2PO_3(Cl^-)_2)_{0.25} \cdot (HPO_3)_{1.50}$ The material is amorphous. Infra red and $^{31}P$ NMR (ppm) are identical to those given in Example 10.

EXAMPLE 13

Zirconyl chloride (octahydrate) (0.151 g, 0.47 mmol.) is dissolved in 10 mLs water and 50% hydrofluoric acid (0.079 g, 1.9 mmol.) is added. 1,1'-bisphosphonoethyl-bipyridinium dichloride (0.105 g, 0.24 mmol.) and methyl phosphonic acid (0.045 g, 0.47 mmol.) are dissolved in 10 mLs of water and this solution is added to the aqueous zirconium solution. The reaction is refluxed for seven days and the white crystalline product is filtered, washed with water, methanol, and acetone, and air-dried to yield the mixed complex:

$Zr(O_3PCH_2CH_2\text{-bipyridinium-}CH_2CH_2PO_3(Cl^-)_2)_{0.5} \cdot (CH_3PO_3)_{1.0}$ The material is amorphous. Infra red analysis is as follows: (IR (cm–1), 3450, 3133, 3056, 2922, 1633, 1555, 1499, 1450, 1309, 1168, 1027, 823, 781, 527).

EXAMPLE 14

In a similar fashion to that described in Example 8, 0.93 mmol. of zirconyl chloride, 0.34 mmol. of 1,1'-bisphosphonoethyl-bipyridinium dichloride, and 0.90 mmoles of 3-aminoethylphosphonic acid are heated in a bomb at 150° C. Upon isolation as therein described the amorphous mixed complex exhibits the following IR spectra: (IR (cm–1), 3500, 3126, 3055, 1646, 1548, 1499, 1443, 1379, 1154, 1041, 865, 823, 760, 731, 541, 499.

EXAMPLE 15

In a similar fashion to that described in either Example 7 or Example 8, zirconyl chloride, 1,1'-bisphosphonoethyl-bipyridinium dichloride, and a phosphorus-containing coligand as shown in the following table are allowed to react.

| Co-ligand Reagent | mmols. | BPBP* mmols. | ZrOCl$_2$ mmols. | Conditions |
|---|---|---|---|---|
| CH$_3$PO(OH)$_2$ | 0.47 | 0.23 | 0.47 | Ex. 8: 150° C. |
| CH$_3$CH$_2$PO(OH)$_2$ | 1.12 | 0.56 | 1.12 | Ex. 7 |
| CH$_3$CH$_2$CH$_2$PO(OH)$_2$ | 0.94 | 0.47 | 0.94 | Ex. 8: 200° C. |
| CH$_3$CH$_2$CH$_2$PO(OH)$_2$ | 0.83 | 0.41 | 0.80 | Ex. 8: 140° C. |
| HOCOCH$_2$CH$_2$PO(OH)$_2$ | 0.30 | 0.19 | 0.15 | Ex. 8: 110° C. |
| PhenylPO(OH)$_2$ | 1.12 | 0.56 | 1.12 | Ex. 7 |
| ClCH$_2$PO(OCH$_2$CH$_3$)$_2$ | 1.12 | 0.56 | 1.12 | Ex. 7 |
| BenzylPO(OCH$_2$CH$_3$)$_2$ | 0.70 | 0.33 | 0.65 | Ex. 7 |

*BPBP = 1,1'-bisphosphonoethyl-bipyridinium dichloride

Thereby produced are mixed complexes of the formula:

$Zr(O_3PCH_2CH_2\text{-bipyridinium-}CH_2CH_2PO_3(Cl^-)_2)_{0.5} \cdot R^3PO_3$

Data on these products are as follows:

| R$^3$ | X-ray | IR Data |
|---|---|---|
| —CH$_3$ | * | See Ex. 13 |
| —CH$_2$CH$_3$ | d = 10.9Å* | Spectra I |
| —CH$_2$CH$_2$CH$_3$ | d = 11.8Å* | Spectra II |
| —CH$_2$CH$_2$CH$_3$ | d = 13.6Å* | Spectra II |
| —CH$_2$CH$_2$COOH | d = 15.4Å | Spectra III |
| -phenyl | d = 19.7Å* | Spectra IV |
| —CH$_2$Cl | d = 11Å* | Spectra V |
| -benzyl | d = 14.5Å | Spectra VI |

* = Peaks present which are attributable to pure metal bisphosphonate.

Spectra I: (IR(cm–1), 3507, 3126, 3056, 2978, 2943, 2887, 1640, 1563, 1506, 1450, 1393, 1281, 1168, 1048, 872, 830, 738, 541.

Spectra II: (IR (cm–1), 3500, 3126, 3049, 2950, 2866, 1633, 1555, 1499, 1450, 1393, 1246, 1041, 872, 823, 795, 731, 541.

Spectra III: (IR (cm–1), 3500, 2915, 1717, 1633, 1415, 1260, 1027, 816, 752, 534.

Spectra IV: (IR (cm–1), 3500, 3126, 3049, 1633, 1555, 1499, 1443, 1386, 1161, 1055, 865, 823, 749, 731, 710, 541.

Spectra V: (IR (cm–1), 3500, 3119, 3049, 1633, 1555, 1499, 1443, 1386, 1161, 1055, 865, 823, 759, 731, 710, 541.

Spectra VI: (IR (cm–1), 3500, 3126, 3056, 1633, 1598, 1492, 1450, 1386, 1253, 1161, 1034, 830, 781, 738, 696, 626, 541, 499.

EXAMPLE 16

$Zr(O_3PCH_2CH_2\text{-bipyridinium-}CH_2CH_2PO_3(Cl^-)_2)0.5(O_3POH)$

The complex prepared as in Example 7 (0.05 g) is stirred with 10 mLs of a 10 mM aqueous solution of dipotassium platinum tetrachloride at room temperature for two days. Over the course of the reaction, the solid changes from white to yellow. The solid then is isolated by filtration, washed extensively with deionized water, and air dried. The solid is suspended in deionized water and hydrogen gas bubbled through the mixture for ten hours. The solid changes from yellow to dark purple. The solid is isolated by filtration, washed with deionized water, and air dried to give a brown solid.

EXAMPLE 17

A substrate of gold deposited on a chromium metal film in turn deposited on glass is treated first with 3-aminopropyltriethoxysilane and then phosphoryl chloride as previously described and then subjected to the procedure of Example 2 three times to prepare a composition of Formula I in which k is 3.

This composition shows a reversible reduction wave at –0.74 V versus a saturated calomel electrode. In water, it shows an irreversible reduction below –1.4 V versus the same standard electrode.

EXAMPLE 18

Twenty-five milligrams of a composition prepared as set forth in Example 6 in 5 mL of 0.1M disodium ethylenediaminetetraacetic acid as a sacrificial reductant in 1 cm$^2$ cell is irradiated with a 200 Watt Hg/Xe lamp. Levels of hydrogen are measured by gas chromatography. The rate of hydrogen production over 18 hours of photolysis is 0.07 mL/hr. Passing the light through a 330 nm cutoff filter ($\lambda$>330 nm) decreases the rate of hydrogen production by more than an order of magnitude. If the filter is removed the sample photogenerates hydrogen as before. The quantum yield for hydrogen formation (2×moles of H$_2$/moles of photons incident with $\lambda$<330 nm) in this system is 0.008.

What is claimed is:

1. An article comprising a supporting substrate having on its surface a photochemically active film comprising (i) a plurality of a complex of the formula:

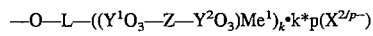

wherein

L is a divalent linking group;

each of Y$^1$ and Y$^2$, independently of the other, is phosphorus or arsenic;

Z is a divalent group containing two conjugated cationic centers which together have a negative E°$_{red}$ value;

Me$^1$ is a trivalent or tetravalent metal of Group III, IVA, or IVB having an atomic number of at least 21 or a lanthanide;

X is an anion;

k has a value of from 1 to about 100; and p has a value of 1 or 2;

wherein each of Y$^1$, Y$^2$, Z, and Me$^1$ may be different for each successive k layer;

wherein each of said complexes is bound to said substrate through the free valence bond on the oxygen atom of the —O—L— component of said complex; and, (ii) colloidal particles of at least one Group VIII metal at zero valence entrapped within said complexes by the Me$^1$ atoms.

2. An article comprising a supporting substrate having on its surface a film, said film comprising:

(i) two or more adjacent metal layers, said metal layers being disposed in substantially spaced, parallel relation to the substrate;

(ii) organic pillars, said pillars being disposed between, and in substantially perpendicular relation to said metal layers, each of said pillars being independently, one from the other, covalently joined to two of said adjacent metal layers and forming interstices between said pillars and said two adjacent metal layers;

(iii) colloidal particles of at least one Group VIII metal at zero valence entrapped within said interstices by said metal layers; and, (iv) linking means binding said substrate to the metal layer closest to the substrate;

wherein each metal layer, independently of the other, comprises atoms of a trivalent or tetravalent metal of Group III, IVA, IVB having an atomic number of at least 21 or atoms of a lanthanide;

wherein said organic pillars are illustrated by the formula:

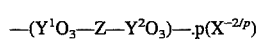

each of Y$^1$ and Y$^2$, independently of the other, is phosphorous or arsenic;

Z is an electron accepting divalent group containing two conjugated cationic centers which together have a negative E°$_{red}$ value, wherein Z is capable of alternating between a stable reduced form and a stable oxidized form;

X is an anion; and, p has a value of 1 or 2.

3. An article according to claim 2, wherein each metal layer, independently of the other, comprises atoms of titanium, zirconium, hafnium, germanium, tin, or lead;

wherein said organic pillars are illustrated by the formula:

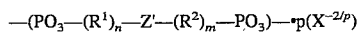

Z' is a divalent aromatic group containing at least two conjugated tetravalent nitrogen atoms;

each of n and m, independently of the other, has a value of 0 or 1;

each of R$^1$ and R$^2$, independently of the other, is a straight or branched divalent alkane chain of six or less carbon atoms;

X is an anion;

the number of said metal layers is from 2 to about 100; and, p has a value of 1 or 2.

4. An article according to claim 2 wherein said colloidal particles of Group VIII metal at zero valence are platinum or palladium.

5. An article according to claim 2 wherein Z is

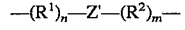

in which

Z' is a divalent aromatic group containing at least two conjugated tetravalent nitrogen atoms;

each of n and m, independently of the other, has a value of 0 or 1; and each of R$^1$ and R$^2$ independently of the other, is a divalent aliphatic or aromatic hydrocarbon group.

6. An article according to claim 5 wherein in Z', each tetravalent nitrogen atom is a ring member in separate aromatic ring systems which ring systems are joined to one another directly or through a conjugated hydrocarbon chain.

7. An article according to claim 6 wherein each aromatic ring system is a monocycle or fused polycycle comprising a pyridine, pyrazine, or pyrimidine ring each of which monocycle or fused polycycle is unsubstituted or substituted with alkyl of 1 to 6 carbon atoms.

8. An article according to claim 5 wherein in Z', both tetravalent nitrogen atoms are ring members in a fused polycyclic aromatic system.

9. An article according to claim 8 wherein the fused polycyclic aromatic system comprises two members independently selected from the group consisting of pyridine, pyrazine, and pyrimidine, said fused polycyclic aromatic system being unsubstituted or substituted with alkyl of 1 to 6 carbon atoms.

10. An article according to claim 5 wherein each of n and m is 1 and each of R$^1$ and R$^2$, independently of the other is a straight or branched divalent alkane chain of six or less carbon atoms.

11. An article according to claim 2 wherein said metal atoms are titaninum, zirconium, hafnium, germanium, tin, or lead.

12. An article according to claim 11 wherein said metal atoms are zirconium.

13. An article according to claim 2 wherein each of $Y^1$ and $Y^2$ is phosphorus.

14. An article according to claim 2 wherein the number of said metal layers is from 2 to 50.

15. An article according to claim 2 wherein said film comprises (i) a plurality of a complex of the formula:

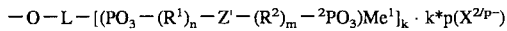

wherein

L is a divalent linking group;

Z' is a divalent aromatic group containing at least two conjugated tetravalent nitrogen atoms;

each of n and m, independently of the other, has a value of 0 or 1; and each of $R^1$ and $R^2$, independently of the other, is a straight or branched divalent alkane chain of six or less carbon atoms;

$Me^1$ is titanium, zirconium, hafnium, germanium, tin, or lead;

X is anion;

k has a value of from 1 to about 100; and p has a value of 1 or 2; and (ii) colloidal particles of zero valence platinum or palladium are entrapped within said complexes by the $Me^1$ atoms.

16. An article comprising a supporting substrate having on its surface a film comprising a plurality of a complex of the formula:

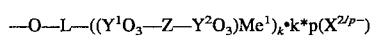

wherein

L is a divalent linking group;

each of $Y^1$ and $Y^2$, independently of the other, is phosphorus or arsenic;

Z is a divalent group which reversibly forms a stable reduced form, said group containing two conjugated cationic centers which together have a negative $E°_{red}$ value and;

$Me^1$ is a trivalent or tetravalent metal of Group III, IVA, or IVB having an atomic number of at least 21 or a lanthanide;

X is an anion;

k has a value of from 1 to about 100; and p has a value of 1 or 2 wherein each of said complexes is bound to said substrate through the free valence bond on the oxygen atom of the —O—L— component of said complex.

17. An article comprising a supporting substrate having on its surface a film, said film comprising:

(i) two or more adjacent metal layers, said metal layers being disposed in substantially spaced, parallel relation to the substrate;

(ii) organic pillars, said pillars being disposed between, and in substantially perpendicular relation to said metal layers, each of said pillars being independently, one from the other, covalently joined to two of said adjacent metal layers and forming interstices between said pillars and said two adjacent metal layers; and, (iii) linking means binding said substrate to the metal layer closest to the substrate;

wherein each metal layer, independently of the other, comprises atoms of a trivalent or tetravalent metal of Group III, IVA, IVB having an atomic number of at least 21 or atoms of a lanthanide;

wherein said organic pillars are illustrated by the formula:

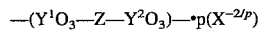

each of $Y^1$ and $Y^2$, independently of the other, is phosphorous or arsenic;

Z is an electron accepting divalent group containing two conjugated cationic centers which together have a negative $E°_{red}$ value, wherein Z is capable of alternating between a stable reduced form and a stable oxidized form;

X is an anion; and, p has a value of 1 or 2.

18. An article according to claim 17 wherein Z is

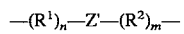

which

Z' is a divalent aromatic group containing at least two conjugated tetravalent nitrogen atoms;

each of n and m, independently of the other, has a value of 0 or 1; and each of $R^1$ and $R^2$, independently of the other, is a divalent aliphatic or aromatic hydrocarbon group.

19. An article according to claim 18 wherein in Z', each tetravalent nitrogen atom is a ring member in separate aromatic ring systems which ring systems are joined to one another directly or through a conjugated hydrocarbon chain.

20. An article according to claim 19 wherein each aromatic ring system is a monocycle or fused polycycle comprising a pyridine, pyrazine, or pyrimidine ring each of which monocycle or fused polycycle is unsubstituted or substituted with alkyl of 1 to 6 carbon atoms.

21. An article according to claim 20 wherein in Z', both tetravalent nitrogen atoms are ring members in a fused polycyclic aromatic system.

22. An article according to claim 20 wherein the fused polycyclic aromatic system comprises two members independently selected from the group consisting of pyridine, pyrazine, and pyrimidine, said fused polycyclic aromatic system being unsubstituted or substituted with alkyl of 1 to 6 carbon atoms.

23. An article according to claim 18 wherein each of n and m is 1 and each of $R^1$ and $R^2$, independently of the other, is a straight or branched divalent alkane chain of six or less carbon atoms.

24. An article according to claim 17 wherein said metal atoms are titanium, zirconium, hafnium, germanium, tin, or lead.

25. An article according to claim 21 wherein said metal atoms are zirconium.

26. An article according to claim 17 wherein each of $Y^1$ and $Y^2$ is phosphorus.

27. An article according to claim 17 wherein the number of said metal layers is from 2 to 50.

28. An article of the formula:

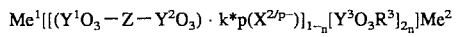

wherein each of $Y^1$, $Y^2$, and $Y^3$, independently of the other, is phosphorus or arsenic;

Z is a divalent group which reversibly forms a stable reduced form, said group containing two conjugated cationic centers which together have a negative $E°_{red}$ value;

each of $Me^1$ and $Me^2$ is a trivalent or tetravalent metal of Group III, IVA, or IVB having an atomic number of at least 21 or a lanthanide;

X is anion;

n has a value of from 0 to 0.8; and p has a value of 1 or 2; and $R^3$ is a nonreducible capping group.

29. An article comprising:
(i) two or more adjacent metal layers, said metal layers being disposed in substantially spaced, parallel relation to each other;
(ii) organic pillars, said pillars being disposed between, and in substantially perpendicular relation to said metal layers, each of said pillars being independently, one from the other, covalently joined to two of said adjacent metal layers and forming interstices between said pillars and said two adjacent metal layers; and,
(iii) organic ligands, said ligands being disposed between said metal layers and between said pillars, each of said ligands being independently, one from the other, covalently joined to one of said adjacent metal layers;

wherein each metal layer, independently of the other, comprises atoms of a trivalent or tetravalent metal of Group III, IVA, IVB having an atomic number of at least 21 or atoms of a lanthanide;

wherein said organic pillars are illustrated by the formula:

$$-(Y^1O_3-Z-Y^2O_3)-•p(X^{-2/p})$$

each of $Y^1$ and $Y^2$, independently of the other, is phosphorous or arsenic;

Z is an electron accepting divalent group containing two conjugated cationic centers which together have a negative $E°_{red}$ value, wherein Z is capable of alternating between a stable reduced form and a stable oxidized form;

X is an anion; and, p has a value of 1 or 2 wherein said ligands are illustrated by the formula:

$$-Y^3O_3-R^3$$

$Y^3$ is phosphorous or arsenic; and, $R^3$ is a non-reducible capping group.

30. An article according to claim 29 wherein Z is $$-(R^1)_n-Z'-(R^2)_m-$$

in which

Z' is a divalent aromatic group containing at least two conjugated tetravalent nitrogen atoms;

each of n and m, independently of the other, has a value of 0 or 1; and each of $R^1$ and $R^2$, independently of the other, is a divalent aliphatic or aromatic hydrocarbon group.

31. An article according to claim 30 wherein in Z', each tetravalent nitrogen atom is a ring member in separate aromatic ring systems which ring systems are joined to one another directly or through a conjugated hydrocarbon chain.

32. An article according to claim 31 wherein each aromatic ring system is a monocycle or fused polycycle comprising a pyridine, pyrazine, or pyrimidine ring each of which monocycle or fused polycycle is unsubstituted or substituted with alkyl of 1 to 6 carbon atoms.

33. An article according to claim 30 wherein in Z', both tetravalent nitrogen atoms are ring members in a fused polycyclic aromatic system.

34. An article according to claim 33 wherein the fused polycyclic aromatic system comprises two members independently selected from the group consisting of pyridine, pyrazine, and pyrimidine, said fused polycyclic aromatic system being unsubstituted or substituted with alkyl of 1 to 6 carbon atoms.

35. An article according to claim 30 wherein each of n and m is 1 and each of $R^1$ and $R^2$, independently of the other, is a straight or branched divalent alkane chain of six or less carbon atoms.

36. A composition according to claim 28 wherein each of said metal atoms are titanium, zirconium, hafnium, germanium, tin, or lead.

37. An article according to claim 36 wherein each of said metal atoms are zirconium.

38. An article according to claim 28 wherein each of $Y^1$, $Y^2$, and $Y^3$ is phosphorus.

39. An article comprising a supporting substrate having on its surface a photochemically active film, said film comprising a first layer and one or more successive layers, each layer independently of the other comprising:

(i) a plurality of the complex illustrated by the formula $$-[(Y^1O_3-Z-Y^2O_3)Me^1]•p(X^{2/p-})$$

each of $Y^1$ and $Y^2$, independently of the other, is phosphorous or arsenic:

Z is a photochemically active divalent group which can form a stable reduced form, said group containing two conjugated cationic centers which together have a negative $E°_{red}$ value; and, $Me^1$ is a trivalent or tetravalent metal of Group III, IVA, or IVB having an atomic number of at least 21 or a lanthanide;

wherein the plurality of $Me^1$ forms a layer;

X is an anion; and, p has a value of 1, 2 or 3;

wherein the $(Y^1O_3-Z-Y^2O_3)$ parts of said complexes are perpendicular to the substrate and said $Me^1$ layers are parallel to said substrate; and, (ii) colloidal particles of at least one Group VIII metal at zero valance entrapped within said complexes by said metal layer, wherein the first layer is bound to said substrate through a linking group having the formula:

$$-O-L-Me^3$$

wherein L is a divalent linking group; and $Me^3$ is a trivalent or tetravalent metal of Group III, IVA, or IVB having an atomic number of at least 21 or a lanthanide, forming a layer;

where the plurality of $-(Y^1O_3-Z-Y^2O_3)$ of the first layer are covalently bonded to the $Me^3$ layer; and, where the plurality of $-(Y^1O_3-Z-Y^2O_3)$ of each successive layer are covalently bonded to the $Me^1$ layer of the preceding layer.

\* \* \* \* \*